United States Patent [19]

Spears et al.

[11] Patent Number: 5,226,430

[45] Date of Patent: * Jul. 13, 1993

[54] METHOD FOR ANGIOPLASTY

[75] Inventors: J. Richard Spears, Winchester; Donna Bourgelais, Malden, both of Mass.

[73] Assignee: The Beth Israel Hospital, Boston, Mass.

[*] Notice: The portion of the term of this patent subsequent to Jan. 24, 2006 has been disclaimed.

[21] Appl. No.: 705,094

[22] Filed: May 24, 1991

Related U.S. Application Data

[63] Continuation of Ser. No. 561,360, Jul. 31, 1990, Pat. No. 5,019,075, which is a continuation of Ser. No. 225,969, Jul. 29, 1988, abandoned, which is a continuation of Ser. No. 4,780, Jan. 8, 1987, Pat. No. 4,799,479, which is a continuation of Ser. No. 664,156, Oct. 24, 1984, abandoned.

[51] Int. Cl.⁵ .............................. A61M 29/02
[52] U.S. Cl. .......................... 128/898; 606/7; 606/15; 606/28; 606/194; 128/401
[58] Field of Search ........... 606/7, 15, 28, 194, 606/14, 27, 192, 194, 162; 128/401, 898; 604/96

[56] References Cited

U.S. PATENT DOCUMENTS

| | | | |
|---|---|---|---|
| 2,078,686 | 4/1937 | Rowe | 128/401 X |
| 2,168,427 | 8/1939 | McConkey | 128/401 X |
| 2,466,042 | 4/1949 | Reich et al. | 128/401 |
| 2,734,508 | 2/1956 | Kozinski | 128/401 |
| 3,494,354 | 2/1970 | Yokota et al. | |
| 3,557,783 | 1/1971 | Castner | |
| 3,661,148 | 5/1972 | Kolin | |
| 3,866,599 | 2/1975 | Johnson | |
| 4,085,757 | 4/1978 | Pevsner | |
| 4,207,874 | 6/1980 | Choy | |
| 4,254,774 | 3/1981 | Boretos | |
| 4,261,339 | 4/1981 | Hanson et al. | |
| 4,266,549 | 5/1981 | Kimura | |
| 4,271,839 | 6/1981 | Fogarty et al. | |
| 4,273,128 | 6/1981 | Lary | |
| 4,307,722 | 12/1981 | Evans | |
| 4,311,146 | 1/1982 | Wonder | |
| 4,313,989 | 11/1983 | Schjeldahl et al. | |
| 4,315,342 | 2/1982 | Ash | |
| 4,315,512 | 2/1982 | Fogarty | |
| 4,318,410 | 3/1982 | Chin | |
| 4,323,071 | 4/1982 | Simpson et al. | |
| 4,384,584 | 5/1983 | Chen | |
| 4,403,617 | 9/1983 | Tretinyak | |
| 4,448,188 | 5/1984 | Loeb | |
| 4,449,528 | 5/1984 | Auth et al. | |
| 4,467,790 | 8/1984 | Schiff | |
| 4,470,407 | 9/1984 | Hussein | |
| 4,512,762 | 5/1985 | Spears | |
| 4,522,205 | 6/1985 | Taylor et al. | |
| 4,612,938 | 8/1986 | Dietrich et al. | |
| 4,646,737 | 3/1987 | Hussein et al. | |
| 4,662,368 | 5/1987 | Hussein et al. | |
| 4,662,383 | 5/1987 | Sogawa et al. | |
| 4,672,962 | 6/1987 | Hershenson | |
| 4,672,969 | 6/1987 | Dew | |
| 4,676,258 | 6/1987 | Inokuchi et al. | |
| 4,799,479 | 1/1989 | Spears | |

FOREIGN PATENT DOCUMENTS 8107379 3/1981 France .
8303188 9/1983 World Int. Prop. O. .

OTHER PUBLICATIONS

Abela, Dec. 1982 "Effects of Carbon Dioxide,
(List continued on next page.)

Primary Examiner—Michael H. Thaler
Attorney, Agent, or Firm—Lorusso & Loud

[57] ABSTRACT

The region surrounding the balloon utilized in percutaneous transluminal coronary angioplasty is heated by means within the balloon or within the skin of the balloon upon inflation of the balloon such that disrupted tissues of the plaque in the arterial wall are heated in order to fuse together fragmented segments of tissue and to coagulate blood trapped within dissected planes of tissue and within fissures created by wall fracture such that upon subsequent balloon deflation a smooth cylindrically-shaped channel results, thereby to prevent collapse of any flap of material which could cause either abrupt arterial closure and an acute myocardial infarction or gradual restenosis at the site of balloon inflation.

7 Claims, 6 Drawing Sheets

OTHER PUBLICATIONS

Nd-YAG, and Argon Laser Radiation on Coronary Atheromateous Plaques," 50 *Amer. J. Cardiology* No. 6, 1199–1205.

Abela, Oct. 1983; "Laser Radiation: Immediate and Long-Term Effect on the Arterial Wall," *Fifth Int'l Cong. on Laser Med. and Surg.* 165, Abstract No. 224.

Abela, Jun. 1984 "Laser Radiation: The Long-Term Effects on Atherosclerotic Arteries," *Amer. Soc. for Laser Med. and Surg. Abstracts* 357, Abstract No. 159.

Abergel, May 1985 "Laser Welding of Skin Wounds," 5 *Lasers in Surgery and Medicine* No. 2, 138, Abstract No. 138.

Armelin, Nov. 1981 "Laser Beam Vascular Anastomosis: An Alternative for Classical Surgical Suture," American Heart Association's 54th Scientific Sessions, Dallas Texas Abstract No. 232.

Bozinis, Oct. 1983 "The Use of Laser Radiation in Cardiovascular Surgery," *Fifth Int'l Cong. of Laser Med. and Surg.* 164, Abstract No. 221.

Choy, Dec. 1982, "Laser Coronary Angioplasty: Experience with 9 Cadaver Hearts," 50 *Amer. J. Cardiology* No. 6, 1209–11.

Choy, Dec. 1982, "Transluminal Laser Catheter Angioplasty" 50 *Amer. J. Cardiology* No. 6, 1206–08.

Choy, Oct. 1983; "Update on Laser Angioplasty," *Fifth Int'l Cong. of Laser Med. and Surg.* 164, Abstract No. 222.

Choy, Jun. 1984, "Laser Angioplasty: Additional Experience" *Amer. Soc. for Laser Med. and Surg Abstracts* 361 Abstract No. 170.

Choy Jun. 1984, "Laser Coronary Recanalization in Human Patients" *CLEO Abstracts,* Abstract No. FL6.

Choy, Jun. 1984, "Update on Laser Recanalization" *Amer. Soc. for Laser Med. and Surg. Abstracts* 357–58, Abstract No. 161.

Clarke, Jun. 1984 "Identification of Photoproducts Liberated by In Vitro Laser Irradiation of Atherosclerotic Plaque Calcified Valves, and Myocardium," *Amer. Soc. for Laser Med. and Surg. Abstracts* 358, Abstract No. 163.

Cortis, Jun. 1984 "Laser Effects on Human Aorta Induced by Steel Tipped Fiber," *Amer. Soc. for Laser Med. and Surg. Abstracts* 358, Abstract No. 162.

Davi, Oct. 1983 "Laser Effects on Vascular Tissues and Occlusive Disease" *Fifth Int'l Cong. for Laser Med. and Surg.* 164, Abstract No. 220.

Dew, 1983, "Laser Microsurgical Repair of Soft Tissue: An Update and Review," 3 *Lasers in Surgery and Medicine,* No. 2, 134.

Dew, 1983, "Laser Assisted Microsurgical Vessel Anastomosis Techniques: The Use of Argon and $CO_2$ Lasers" 3 *Lasers in Surgery and Medicine* No. 2, 135, Abstract No. 113.

Dew Jun. 1984, "Laser Microsurgical Repair of Soft Tissue: A Demonstration of Surgical Techniques," *Amer. Soc. for Laser Med. and Surg Abstracts* 351, Abstract No. 140.

Dougherty, 1979 "Photoradiation in the Treatment of Recurrent Breast Carcinoma," *Cancer Therapy Abstracts* No. 79-0299, 69.

Dries, Jun. 1984 "Variable Responses of Atherosclerotic Aorta to Argon Laser," *Amer. Soc. for Laser Med and Surg. Abstracts* 359, Abstract No. 166.

Eugene, Jun. 1984 "Plaque Removal from Atheromatous Blood Vessels in Rabbits," *Amer. Soc. for Laser Med. and Surg. Abstracts* 357, Abstract No. 160.

Fasano, Jun. 1984 "Delayed Histological Effects of the Laser on the Arterial Vessel Walls," *Amer. Soc. for Laser Med. and Surg. Abstracts,* 313, Abstract No. 18.

Geschwinn, Nov. 12, 1983 "Laser Angioplasty: Effects on Coronary Artery Stenosis," *The Lancet* 1134.

Gollan, Oct. 1975 "Oxygen Transport of Colloidal Fluorocarbon Suspensions in Asanguineous Rabbits" 229 *American J. Physiology* 1045–49.

Gorisch, 1982 "Heat-Induced Contraction of Blood Vessels" *Lasers in Surgery and Medicine* No. 2 1–13.

Gruntzig, Jul. 12, 1979 "Nonoperative Dilatation of Coronary-Artery Stenosis," 301 *New England Journal of Medicine* No. 2, 61–68.

Hecht, Apr. 1986, "Laser Angioplasty: Success Remains Elusive" *Lasers & Applications,* pp. 32–36.

Jain, Jun. 1984, "Sutureless Anastomosis . . . ", *Amer. Soc. for Laser Med. and Surg. Abstracts* 352, Abstract No. 144.

Jain, Jun. 1984, "Laser Angioplasty . . . ", *Amer. Soc. for Laser Med and Surg. Abstracts* 359, Abstract No. 165.

Kanter, Aug. 1981, "Superiority of Perfluorocarbon Cardioplegia . . . " 64 *Circulation* Supp. II, 11-75–11-80.

Krueger, 1985, "Argon Laser Coagulation of Blood for the Anastomosis of Small Vessels", *Lasers in Surgery and Medicine* No. 5, 55–60.

Lawrence, Jun. 1984, "Morpholgic Changes of Argon Lasers . . . ", *American Soc. for Laser Med. and Surg. Abstracts* 360, Abstract No. 167.

(List continued on next page.)

OTHER PUBLICATIONS

Ledor, Jun. 1984, "Vascular Angioscopy and Laser Angioplasty", *Amer Soc. for Laser Med. and Surg. Abstracts*, 361, Abstract No. 171.

Lee, Dec. 1981, "Laser-Dissolution . . . ", *Amer. Heart J.* 1074–1075.

Lee, Oct. 1983, "The Use of Dual Fiberoptic Catheter . . . ", *Fifth Inter. Cong. of Laser Med. and Surg.* 165, Abstract No. 233.

Lee, Jul. 1, 1985, "Limitations, Risks and Complications . . . ", 56 *Amer. J. Cardiology* 181–85.

Linsker, 1984, "Far-Ultraviolet Laser Ablation . . . ", *Lasers in Surgery and Medicine* No. 4, 201–206.

Lipson, 1960, "The Photodynamic Properties of . . . ", 85 *Archives of Dermatology* 76/508–84/516.

Lipson, Jan. 1961, "The Use of a Derivative . . . ", 26 *J. Nat'l Cancer Inst.* 1–8.

Lipson, Dec. 1967, "Hematoporphyrin Derivative for . . . ", 20 *Cancer* 2255–57.

Moan, 1979, "The Mechanism of Photodynamic Inactivation . . . ", *Cancer Therapy Abstracts* No. 79–2363, 735–36.

Mohan, Jan. 1982 "Aqueous Peroxyoxalate Chemiluminescense: Final Report to the Office of Naval Research" 1–156, Contract N00014 77–C–0634 Amer. Cyanamid Co., Discovery Research Dept., Chem. Research Div., Bound Brook NJ.

Protell, Feb. 1978 "The Heater Probe: A New Endoscopic Method . . . " 74 *Gastroenterology* No. 2, Part 1, 257–62.

Quigley, 1985, "Microvascular Anastomosis . . . " *Lasers in Surgery and Medicine* No. 5, 357–65.

Sanderson, Nov. 1972, "Hematoporphyrin as a Diagnostic Tool", 30 *Cancer* 1368–1372.

Sauer, May 1985, "Bursting Pressures of $CO_2$ . . . " 5 *Lasers in Surg. and Med.* No. 2, 149, Abstract No. 44.

Serur, "Laser Balloon Angioplasty . . . ", 72 *Circulation* III–457 Abstract No. 1825 Published 1985.

Sery, 1979 "Photodynamic Killing . . . ", *Cancer Therapy Abstracts* No. 79–0463, 160–61.

Spears, 1983, "Fluorescence of Experimental Atheromatous . . . " 71 *J. Clin. Investigation* 395–399.

Spears, 1983, "Vivo Coronary Angioplasty", 1 *J. Amer. Coll. Cardiology* 1311–14.

Spears, 1985, "Coronary Angioplasty During Cardiac . . . ", 6 *J. Amer. Coll of Cardiology* No. 1, 93–97.

Spears, 1986, "Potential Role of Lasers in the Cardiad . . . ", *Cardiac Catherization and Angioplasty* 3rd Ed., Grossman Ed., 536–64.

C. Thomas, Jun. 1984, "Sutureless Microvascular Extra-Intracranial Anastomosis with Nd:YAG Laser" *Amer. Soc. for Laser Med. and Surg. Abstracts* 311–12, Abstract No. 15.

Van Gemert, May 1985, "Modeling Of Laser-Tissue Welding . . . " 5 *Lasers in Surgery and Medicine* No. 2, 171, Abstract No. 112.

Ward, 1984, "Laser Recannalization of Atheromateous Vessels . . . " *Lasers in Surgery and Medicine* No. 4, 353–63.

White, 1985, "Biological Effects of Laser Welding . . . ", 5 *Lasers in Surgery and Medicine* No. 2, 146 Abstract No. 37.

Wolinsky, "Atherosclerosis", XIV *Cardiovascular Disease 1218–22*.

OPTICAL DIFFUSING
TIP, 32

METHOD FOR ANGIOPLASTY

This is a continuation of copending application(s) Ser. No. 07/561,360 filed on Jul. 31, 1990 now U.S. Pat. No. 5,019,075, which is a file wrapper continuing application of Ser. No. 225,969 filed Jul. 29, 1988; abandoned which is a continuation of 004,780 filed Jan. 8, 1987 (now U.S. Pat. No. 4,799,479); which is a file wrapper continuing application of Ser. No. 664,156 filed Oct. 24, 1984 abandoned.

FIELD OF THE INVENTION

This invention relates to angioplasty and, more particularly, a method and apparatus for preventing abrupt reclosure and restenosis after treatment.

BACKGROUND OF THE INVENTION

The mortality and morbidity from ischemic heart disease results primarily from atheromatous narrowings of the coronary arteries. Although various medical and surgical therapies may improve the quality of lifestyle of most patients with symptomatic coronary atherosclerosis, these therapies do not favorably change the underlying anatomy responsible for the coronary luminal narrowings and therefore do not prevent the occurrence of future cardiac events such as occurrence of worsening of signs and symptoms of myocardial ischemia, myocardial infarction and sudden death.

Percutaneous transluminal coronary angioplasty (PTCA) has recently been developed as an alternative method of treatment of coronary atherosclerosis. During cardiac catherization an inflatable balloon is inserted in a coronary artery at the region of a coronary narrowing. Inflation of the balloon for 15-60 seconds results in expansion of the narrowed lumen or passageway. Because residual narrowing is usually present after the first balloon inflation, multiple inflations are routinely performed in an attempt to reduce the severity of the residual stenosis or tube narrowing. Despite these multiple inflations, a mild to moderately severe residual stenosis usually is present after successful PTCA.

One of the major problems with such treatment is that a flap of material occasionally is formed during the treatment which, after withdrawal of the instrumentation, falls back into the artery causing abrupt reclosure. This necessitates emergency coronary artery bypass surgery and thus PTCA is potentially dangerous and often provides only a temporary treatment of symptoms of obstructive coronary arterial atherosclerosis. The reason that the flap is formed is that upon balloon inflation the surrounding material is broken or fragmented which causes blood to enter the arterial wall between planes of dissection. This causes the arterial wall to swell acutely and either reduces the size of the channel or completely obliterates the channel resulting in a five percent incidence of abrupt reclosure.

Moreover with present PTCA procedures, postmortem pathologic studies show that disruption of the arterial wall and atheromatous plaque occurs following balloon inflation, including fracture of the plaque and separation of tissue layers, e.g., dissection. Angiographically a shaggy or hazy appearance of the coronary lumen is often seen and evidence for overt dissection is often apparent following successful PTCA. Disruption of the arterial wall temporarily increases the size of the coronary channel but predisposes to deposition of platelets and microthrombi which very likely contribute to the greater than 25% incidence of restenosis within three to six months following successful PTCA.

By way of further background, recent studies have been reported using lasers to perform vascular anastomoses so that end-to-end and end-to-side arterial and vein grafting can be achieved without sutures. The basic principle simply involves placing the free edges of a vessel and the graft in close proximity and heating these tissues with either an argon-ion, neodymium-:YAG, or $CO_2$ laser. Cross linking of collagen and other tissue proteins occurs and a coagulation is observed pathologically following the treatment. The tissue integrity is maintained, however, and the tensile strength of the "sutureless" anastomosis rivals that of anastomoses performed with sutures used in a conventional manner. Moreover, short and long term tissue healing appears to be better with the laser thermal fusion of tissues than with the suture technique.

SUMMARY OF THE INVENTION

The subject technique reduces the disruption of the arterial wall and therefore the complications associated with PTCA. During balloon inflation the disrupted tissues of the plaque and the arterial wall are heated in order to fuse together fragmented segments of tissue and to coagulate blood trapped within dissected planes of tissue and within fissures created by wall fracture. Upon subsequent balloon deflation, a smooth, cylindrically-shaped channel results. The thermal energy is applied either during the first balloon inflation or during a balloon inflation subsequent to PTCA performed in a routine manner.

It has been found that by using the subject technique thermal fusion of fragmented segments of the arterial wall following PTCA is possible. Moreover, it has been found that a better "set" of the vessel wall occurs. Elastic recoil of portions of the arterial wall, which often occurs following conventional PTCA is reduced with the subject thermal treatment. The smooth luminal surface results in normal patterns of blood flow such that local turbulence and regions of flow separation and stagnation, which favor platelet deposition, thrombus formation, and plaque growth, are reduced. Abrupt reclosure following the thermal treatment during PTCA does not occur since upon balloon deflation blood is unable to enter dissected planes within the arterial wall. The incidence of restenosis is reduced because of more favorable flow patterns produced by the smooth lumen and because the fused necrotic elements of the arterial wall are incapable of proliferation in response to the initial injury sustained during balloon inflation. Moreover, while it has been suggested that the smooth muscle cell, the principal cell type within the plaque and normal arterial wall, proliferates in response to any form of injury and contributes to plaque progression, thermal destruction of the smooth muscle cell provided by the subject technique prevents this response.

Thus one aspect of the present invention is the application of thermal energy to the arterial wall during PTCA. This energy is applied principally to either the atheromatous plaque, the normal arterial wall, blood within the arterial wall or to all three tissues simultaneously.

The present invention relates to a method of balloon angioplasty which is based on the following novel combination of observations: First, thermal energy can be used to fuse together disrupted tissue elements of the arterial wall following conventional balloon angioplasty; secondly, that blood is an effective absorber of many wavelengths of light, including the 1.06 micron radiation of the neodymium:YAG laser and that the presence of blood within arterial wall fissures created by a conventional balloon angioplasty will facilitate laser fusion of disrupted plaque and other arterial wall elements; thirdly, that application of tissue pressure during application of thermal energy facilitates fusion of disrupted tissue elements and, therefore, that balloon inflation during application of thermal energy is useful and necessary for compression of the disrupted tissue layers; fourthly, that balloon inflation during application of thermal energy will prevent constriction of the lumen cross section from tissue shrinkage; fifthly, that application of thermal energy to the arterial wall during balloon inflation is acutely and chronically well tolerated by arterial wall tissue; and, sixthly, that thermal energy can be applied to the arterial wall during balloon inflation without damaging the balloon or causing the formation of intraluminal clots.

Although the most important application of this novel technique is to improve PTCA of coronary arteries, this technique can also be applied to atherosclerotic arteries located elsewhere, such as the renal, iliac, femoral and popliteal arteries.

In addition, this technique may be applied to carotid arteries, unlike conventional angioplasty, because thermal fusion of the disrupted arterial tissues prevents embolization of tissue fragments to the brain.

In a preferred embodiment, the balloon is filled with transparent liquid and the balloon itself is transparent. An optical fiber is utilized within the catheter which has a light disseminating termination within the balloon structure. Laser light is injected into one end of the fiber and is disseminated by the disseminating means at the end of the fiber within the balloon such that the light travels virtually unaffected through the liquid in the balloon and through the balloon itself to the surrounding tissue which contains a certain amount of blood. When utilizing a neodymium:YAG laser at 1.06 microns, it has been found that this radiation while weakly absorbed by the surrounding tissue is strongly absorbed by the blood which causes the required fusion.

In studies of fresh postmortem human atherosclerotic arteries, filled with heparinized blood, it was found that fusion of plaque fragments and plaque-media separations could be easily achieved with this technique without vaporizing any portion of the plaque or normal arterial wall. Histologic examination of formalinfixed arterial specimens subjected to this treatment showed a coagulum at the junction between layers or fragments of tissue, while no overt evidence of damage to the normal arterial wall was found. Moreover, no tissue adhesion to the balloon material occurred, and no damage occurred to the balloon itself, which could be made from one of a variety of high temperature plastic materials, such as a silicone polymer (Silastic), Reynolds oven cooking bags and plastic sheets of autoclave packaging material.

The thermal fusion of disrupted arterial tissues appeared to be facilitated not only by preferential absorption of the neodymium:YAG radiation by blood between separated tissue layers, but also by the increase in tissue pressure produced first by balloon inflation and second by tissue shrinking from heating, the latter effect very likely representing initial protein cross linking. When arterial tissue is heated to temperatures greater than 70 degrees C., tissue shrinkage will ordinarily occur as a result of cross linking of proteins. However, in the present invention, the fixed volume of fluid within the balloon prevents the lumen cross section from decreasing in size during thermal fusion of tissues. Since the balloon is deflated after completion of thermal fusion, the lumen cross section following balloon deflation is not significantly smaller than the inflated balloon.

The following list describes alternative techniques which can be used to heat the tissues.

The first technique is the heating of the liquid within the balloon of the angioplasty catheter. Any biocompatible liquid used within the balloon, typically a normal saline/radiographic contrast medium mixture, can be heated with one or more electrically heated wires. Alternatively the liquid can be heated by laser energy delivered from one or more optical fibers. In the latter embodiment a biocompatible component of the liquid absorbs the specific laser wavelength used. For example, hemoglobin dissolved or suspended in the liquid strongly absorbs the energy of an argon-ion laser. As a result the liquid heats rapidly. Other examples of biocompatible pigments, which can be used in a similar manner, include Evan's Blue, methylene blue and Congo red. If water is used as the absorber, no visible pigments are required. Many different lasers, such as the $CO_2$ laser operating at the 10.6 micron wavelength, can be used to heat water efficiently.

In another embodiment, laser energy transmitted by an optical fiber is used to heat one or more metallic elements, such as wires, within or near the balloon.

In another embodiment, the liquid is heated by a chemical exothermic reaction. Both the reactants and the products are biocompatible. Examples include the dissolution of magnesium sulfate powder or the interaction of silver chloride and sodium hydroxide solutions. The individual components required for the exothermic reaction are injected into the balloon cavity either simultaneously or sequentially.

In another embodiment the balloon is heated directly. As an example, thermal conductive material within the membrane of the balloon is heated directly. In one embodiment, a fine wire meshwork within the substance of the balloon is heated electrically. Alternatively, a meshwork of optical fibers, each of which is "lossy," i.e., each fiber diffuses light along its length, is coupled to the output of a laser. One or more components of the material within the balloon absorb the wavelength of the specific laser used and results in heating the balloon material. In another embodiment, laser energy is used to heat a wire meshwork within the balloon material. In yet another embodiment, the laser energy is delivered to the cavity of the balloon, with the balloon filled with a biocompatible gas such as $CO_2$, the energy being absorbed only by the balloon material, or other absorber(s) provided within the interior of the balloon.

In a still further embodiment, the tissues are heated directly. The plaque, the normal arterial wall, blood within the arterial wall, or any or all of these tissues are heated directly without first heating either the liquid within the balloon or the balloon material. For example, the plaque and any injured portion of the arterial wall, when routine PTCA is performed prior to application of thermal energy during subsequent balloon inflation, may be stained with a dye, such as Evan's Blue or methylene blue. The energy of a Krypton or an argon-ion laser, among other lasers, is absorbed by the pigmented tissue and not by a translucent liquid or gas-filled balloon. Hemoglobin within blood, which has entered the arterial wall or spaces created by fractures from PTCA performed in a routine manner, acts as a natural pigment and is selectively heated by the output of any of a variety of lasers, such as an argon-ion laser.

An additional and optional element of the subject invention is the use of a sound transducer in conjunction with the laser irradiation to sense intra-arterial sound produced by the laser irradiation heating of the tissue. In one embodiment, a catheter sound transducer similar to a high fidelity end-tipped manometer used to measure intravascular blood pressure is positioned within the outer catheter guide sheath near the balloon.

In another embodiment, either the balloon material, fluid or other absorbing substance(s) within the interior of the balloon, the arterial wall tissue(s), including blood, plaque, media, adventitia, either alone or in any combination, or any combination of these absorbing materials are heated by an external source, such as focussed microwave or ultrasonic radiation.

In another embodiment, a sound transducer is placed external to the body on the skin overlying the region of the artery being treated. If the laser radiation or direct heat incident on the plaque through the balloon wall is intense enough to cause vaporization, it has been found that a high frequency acoustic signal is generated which will be picked up by the sound transducer. The laser power is then reduced, either by operator control or automatically if the transducer is connected to an electronic monitoring circuit. A high pass filter, with or without temporal gating with the patient's electrocardiogram, would be used, whether the sound transducer is external to the body or mounted on a catheter, in order to enhance recognition of the high frequency sounds generated by tissue vaporization by suppressing low frequency background noise. Real-time spectral analysis of the acoustic signal could also be performed to enhance recognition of sound generated by tissue vaporization. Similar technology has been used by others to externally record the sound of turbulence of blood within diseased coronary arteries in patients.

In all of the foregoing embodiments, energy in the form of laser radiation or heat is delivered to the entire circumference of the arterial cross section homogeneously along, typically, a 5 to 10 mm length of arterial wall. However, in another embodiment, the laser energy or heat is applied only to discrete locations around the arterial cross section and/or along the length of the artery. One or more of these said locations may be treated either in a random manner or on the basis of which portion of the artery would most likely benefit from the treatment as ascertained from the angiographic appearance of the arterial lumen. When laser radiation is used as described in one embodiment, the diffusing tip is constructed such that radially directed emission of the radiation occurs only at discrete locations along the diffusing tip. In one such embodiment, the surface of the diffusing tip, except for the discrete location, around the tip which permit emission of laser radiation, is coated with a highly reflective material such as gold.

In another embodiment, the diffusing tip consists of the termination of multiple optical fibers at different locations within the balloon. Each fiber, by a variety of means, such as an angled optical cleave, a miniature side-directing lens, or a prism, would emit laser radiation towards a discrete location within the arterial wall. In one embodiment, the laser transmission through each fiber is controlled independently from laser transmission through the other fibers.

The acute and chronic effects of heat in vivo on the normal dog carotid artery have been studied before and after treatment with the subject technique. The arteries subjected to the subject technique were normal and not plaque-filled as is the case in atherosclerosis. The following tests show that if the balloon is inflated in a normal segment of the artery no detrimental effects occur. These tests were conducted as follows: A solution of normal saline containing Congo red was used to fill a medical grade silicone polymer-based balloon catheter and, after introduction of the balloon, the diameter of which ranged from 3 to 5 mm after inflation to a pressure of 3-4 atmospheres, into the lumen of a carotid artery of each anesthetized dog, the solution was heated with an argon-ion laser via an optical fiber which terminated within the balloon. Three to five watts of laser energy was delivered over an approximately 5 to 10 mm length of balloon for one to three minutes. In each dog study, as a control, the contralateral carotid artery was subjected to the same balloon inflation but without application of heat. Surface temperature of the balloon was measured to be 80°-100° C. during laser exposure, while surface temperature of the heated dog arteries was found to be 60°-70° C. within 30 seconds after the onset of laser delivery. Angiographic follow-up in six dogs at one hour, one day, one week, and one month after balloon inflation showed no significant difference in the appearance of the arterial lumen between heated and control arteries, with the exception of one dog which demonstrated a thrombus which had formed between one day and one week after treatment. No anticoagulants were given to any of the dogs after the heat exposure, and it is felt that the delayed thrombus formation in the one dog could have been prevented by daily administration of anticoagulants, such as aspirin and heparin, after the heat treatment. Gross inspection of the arteries of the other animals revealed no pathology such as thrombus, stricture or aneurysm. Microscopic examination of the dog arteries demonstrated no difference in tissue morphology between the heated and control arterial segments. It should be noted that in these normal arteries, balloon inflation caused the arterial wall to stretch evenly, not producing the fissures which are typical of balloon expansion in the presence of more rigid arterial plaque. Without these fissures which fill with and trap blood and become rigidly welded together during heating, no damage is expected until the higher temperatures capable of producing a general coagulation necrosis are reached. No clot formed on the balloon itself after heat exposure, and no evidence of acute thrombosis or embolism occurred in any animal. Thus, not only is the present invention effective in fusing disrupted layers of atherosclerotic tissue following a conventional angioplasty procedure, but also it is operable and safe when practiced in a manner similar to a conventional angioplasty procedure.

BRIEF DESCRIPTION OF THE DRAWINGS

These and other features of the subject invention will be better understood in connection with the detailed description taken in connection with the drawings of which.

DETAILED DESCRIPTION

Figure 1A:
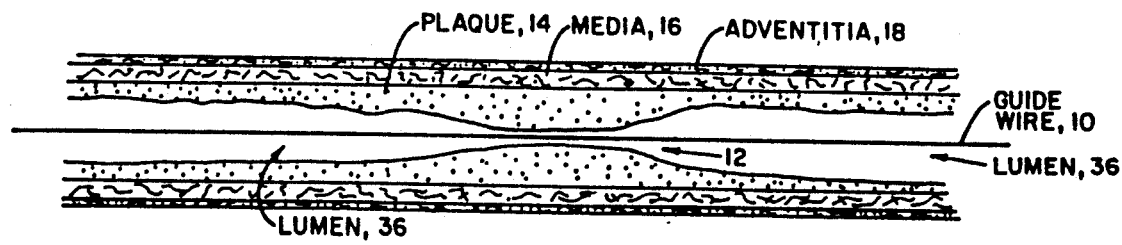
FIGS. 1A-1D are diagrammatic illustrations of a prior art percutaneous transluminal coronary angioplasty procedure in which plaque formed within the coronary artery is fractured initially by the inflation of a balloon catheter and in which after deflation of the balloon and removal of the catheter abrupt reclosure can occur with the flaps of fragmented plaque occluding the coronary artery.
Figure 1B:
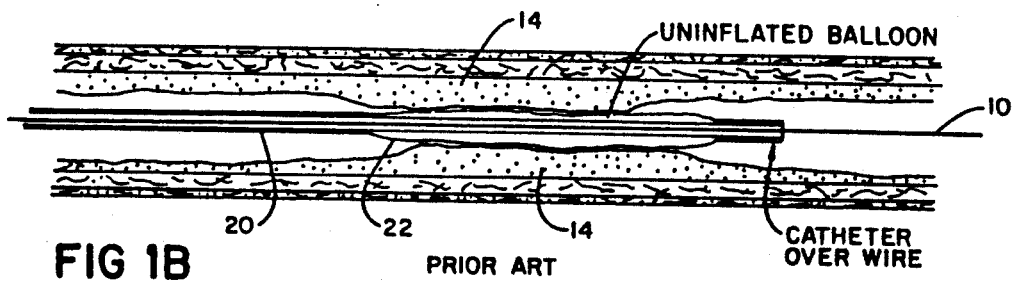
Figure 1C:
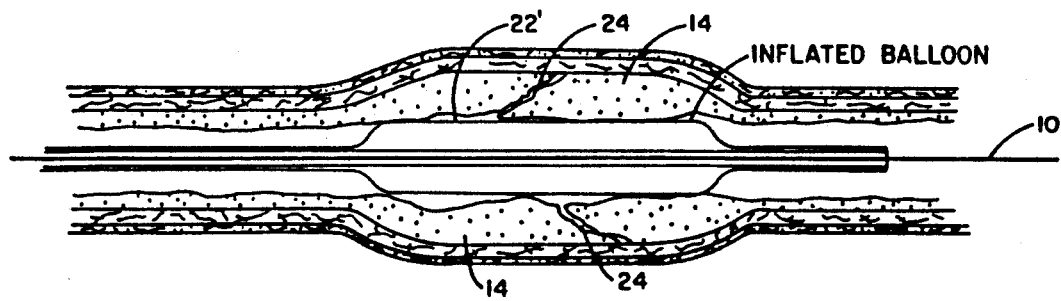
Figure 1D:
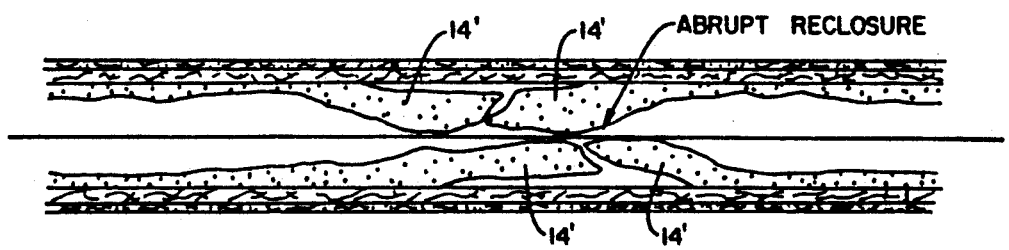

As mentioned hereinbefore, during percutaneous transluminal coronary angioplasty or indeed any type of balloon angioplasty and referring now to FIGS. 1A–1D, in the prior art a guide wire 10 is inserted through the artery and through the region 12 which is occluded primarily by plaque 14 which is surrounded by media 16 and by adventitia 18. It is recognized that it is the plaque which forms the occlusion. In the conventional procedure, a catheter 20 is provided around guide wire 10 which includes a deflated balloon section 22 which surrounds the wire. This balloon section is placed adjacent to plaque 14 and as illustrated in FIG. 1C is inflated as illustrated at 22' which opens up the artery while at the same time providing fissures or dissected planes of tissue 24. As illustrated in FIG. 1D, with the catheter removed, the plaque 14 can collapse into the center of the artery as illustrated by flap portions 14' which results in an abrupt reclosure of the artery that can result in an acute myocardial infarction.

Less severe disruption of the arterial wall commonly results in gradual restenosis within 3 to 6 months after conventional balloon angioplasty because of platelet adhesion to exposed arterial tissue surfaces and because of the presence of regions of blood flow separation and turbulence within the arterial lumen 36, all of which predispose to microthrombi deposition and cellular proliferation within the arterial wall.

Figure 2:
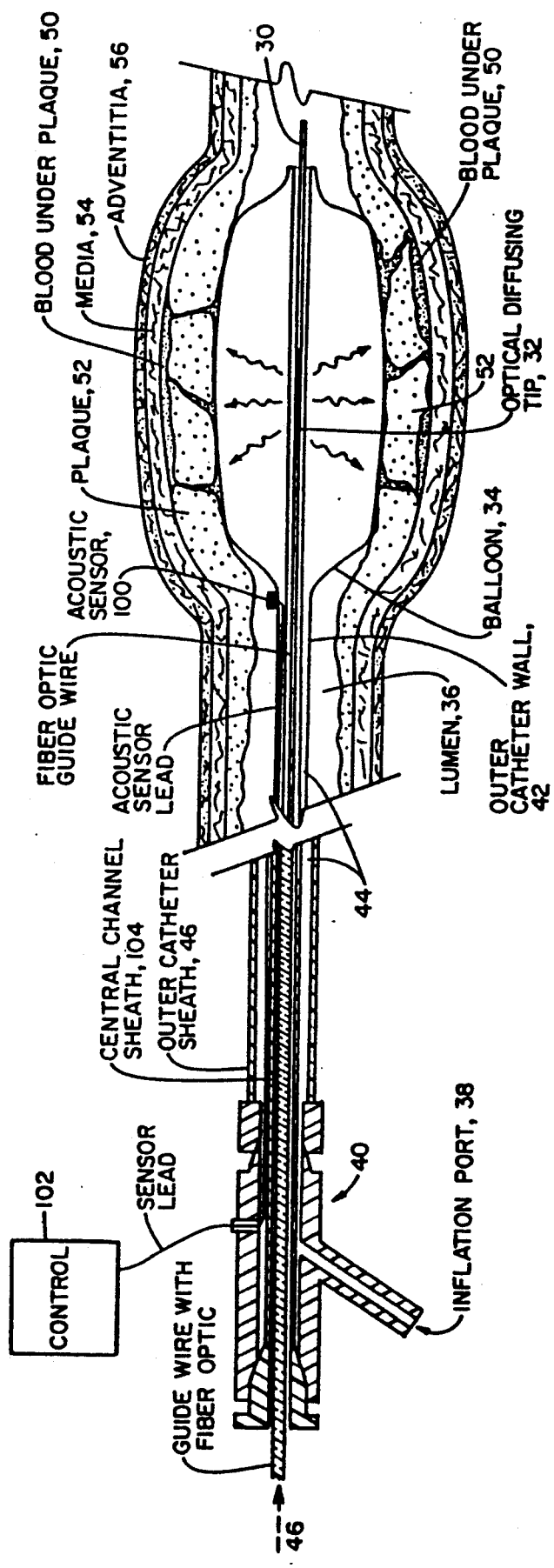
FIG. 2 is a cross-sectional and diagrammatic illustration of one embodiment of the subject invention in which the area immediately surrounding the inflated balloon is fused due to laser radiation which is transmitted through the fluid of the balloon and through the transparent balloon wall to blood within the wall of the coronary artery segment being treated, which heated blood causes the welding of adjacent, disrupted layers throughout the plaque, media and adventitia, resulting in a smooth channel once the balloon is deflated.
Figure 3:
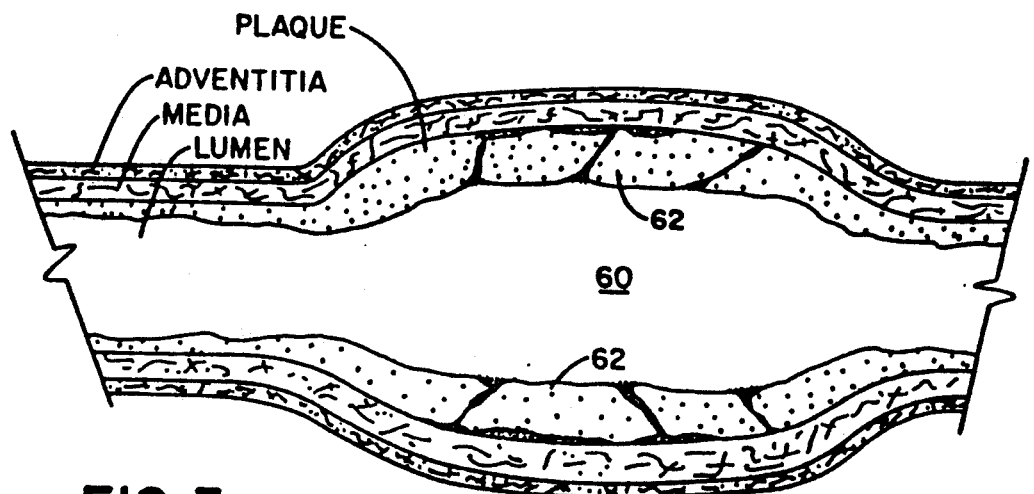
FIG. 3 is a cross-sectional and diagrammatic illustration of the result of utilizing the procedure of FIG. 2 illustrating the channel formed by the fusion which takes place due to fusing produced by heat in the vicinity of the balloon wall.

Referring to FIG. 2 in a preferred embodiment, the usual guide wire is replaced with an optical fiber 30 which has an optical diffusion area or tip 32 midway in the region of an inflated balloon 34 such that, when the catheter is inserted around the optical fiber in lumen 36 and expanded by virtue of providing a transparent fluid through inflation port 38 in termination apparatus generally indicated at 40, the fluid passes through the catheter wall 42 by virtue of a channel 44 in the outer catheter sheath 46 such that balloon 34 is initially inflated. After inflation, laser radiation indicated by dotted arrow 46 is introduced into the optical fiber 30 and is transmitted to the optical diffusion tip 32 where the laser light is diffused and impinges upon blood 50 which usually exists within the arterial wall after fracture or dissection of the plaque has occurred following conventional balloon inflation, with the plaque 52 being held in place upon completion of the fusion process in which disrupted arterial wall elements, media 54 and adventitia 56, are raised to the fusion temperature. The fluid utilized for inflation of the balloon may be contrast medium or crystalloids such as normal saline or 5% dextrose in water and is relatively transparent to the radiation which, in the embodiment shown, is on the order of 1.06 microns which is highly absorbed by the blood. The blood within the arterial wall is therefore heated and this heat radiates to fuse the area immediately surrounding balloon 34 such that as illustrated in FIG. 3 upon removal of the catheter a smooth channel 60 exists with relatively smooth walls 62 and with the surrounding tissue having been fused to prevent the aforementioned reclosure.

The diffusing tip is centrally located within balloon 34 and the length of said tip is typically one half or less the length of the balloon. Thus, tissues at the proximal and distal ends of balloon 34 are not heated, and no thermal injury occurs to blood within lumen 36.

It will be appreciated that a diffusing tip or area along an optical fiber may be provided simply by removing the cladding and abrading the fiber core surface such that the fiber surface is roughened.

Alternatively the diffusing tip 32 can be made of a material which effectively scatters the laser energy and the diffusing tip would then be coupled to the output end of the optical fiber. In another embodiment, the optical fiber lies within channel 44 and terminates directly within the balloon. The diffusing tip 32 in this latter embodiment could be similar in design to diffusing tips of the aforementioned embodiments, but could also be comprised of the fluid used to inflate balloon 34. Examples of biocompatible fluids which would be effective scattering media for laser radiation include dilute lipid emulsions and perfluorochemical emulsions. In other embodiments, the optical fiber would lie within the wall of either the outer catheter sheath 46 or the central channel sheath 104. In yet another embodiment, the central channel sheath 104 is comprised of a hollow optical fiber with a concentric core-cladding arrangement which would terminate in a diffusing tip. Laser energy would then be transmitted within the core of the optical fiber, and the hollow interior of the fiber would allow coaxial placement of a guide wire through the central channel sheath during the laser energy transmission period.

It will be appreciated that the balloon is in the form of a doughnut in cross section which is in essence slipped over the guide wire or optical fiber and inflated when the balloon is in proper position.

As mentioned hereinbefore, the subject procedure may be utilized in place of the conventional percutaneous transluminal coronary angioplasty or may be used subsequent thereto for the purposes of fusion in the area of the angioplasty.

Figure 4:
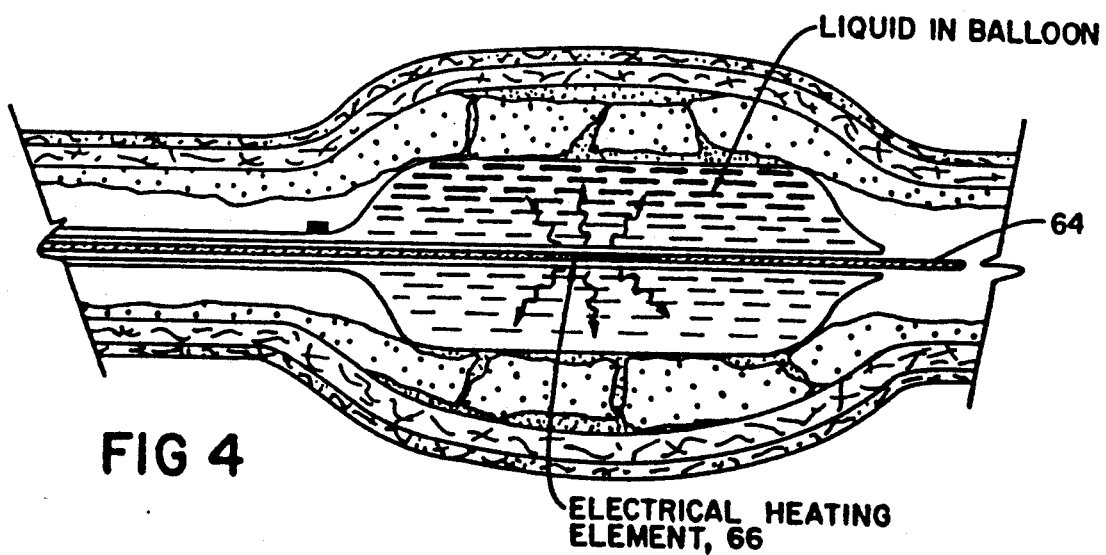
FIG. 4 is a cross-sectional and diagrammatic illustration of an alternative embodiment of the subject invention in which liquid within the balloon is electrically heated, which heat is then utilized in the fusion process to produce the result illustrated in FIG. 3.

Referring to FIG. 4, instead of the utilization of fiber optic transmission of energy to the balloon area, electrical conductors 64 may be utilized as a guide wire in which an electrical heating element 66 is driven from a power source (not shown in this figure) to provide heat to fluid within the balloon which then heats the surrounding tissue to provide the aforementioned fusion. The liquid in this case may be crystalloids or a liquid with a high boiling point such as Dow Corning 550 silicone diluent which transmits the heat from the heating element to the walls of the balloon and then to the tissue immediately surrounding these walls.

Figure 5:
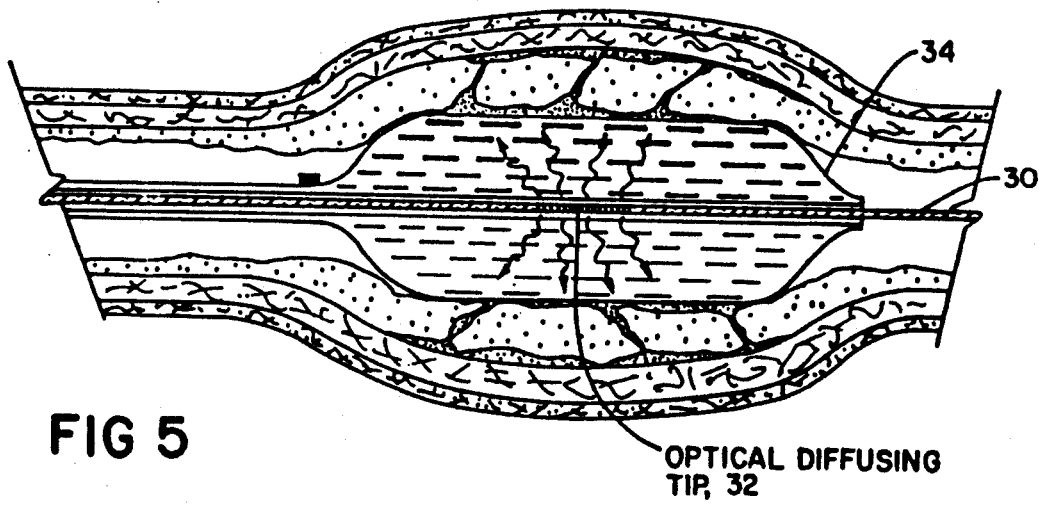
FIG. 5 is a cross-sectional and diagrammatic illustration of a still further embodiment of the subject invention in which liquid within the balloon is heated by laser radiation emanating from an optical diffusing tip thereby to heat the liquid within the balloon for the production of fusion and the result of FIG. 3.

Referring to FIG. 5, a similar result may be obtained by utilizing the optical fiber 30 and optical diffusing tip 32 in which, rather than having a transparent fluid within balloon 34, an absorbing fluid is utilized which absorbs laser energy, normally in the 0.3-10.6 micron range, with the liquid within balloon 34 being selected from the biocompatible group including water, hemoglobin and related pigments such as bilirubin and porphyrins, Congo red, Evan's Blue and methylene blue, and other materials absorbing in this range. The result is similar in that heat is directed to the tissue immediately surrounding the surface of the balloon which causes the aforementioned fusion.

Figure 6:
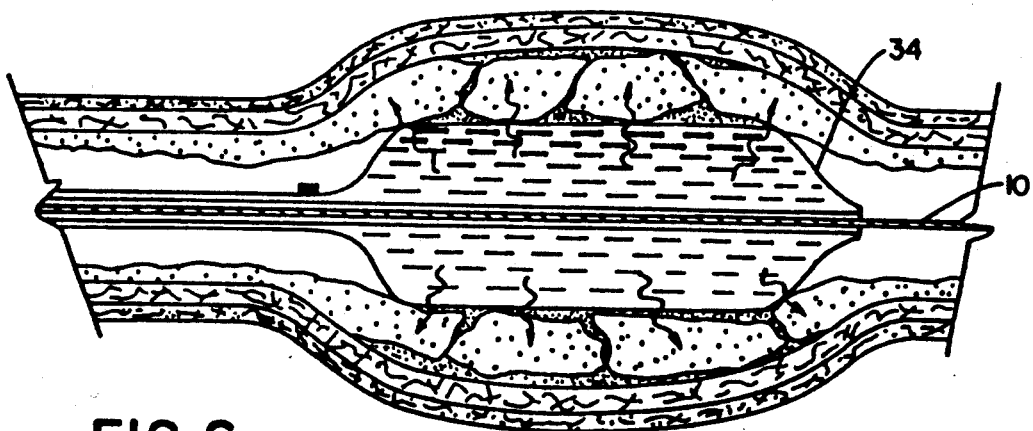
FIG. 6 is a cross-sectional and diagrammatic illustration of a still further embodiment of the subject invention in which heat within the balloon is produced by an exothermic chemical reaction of chemical components pumped into the balloon, with the resulting heat radiating outwardly to produce the fusion result of FIG. 3.

Referring to FIG. 6 and a still further embodiment, heat may be generated within balloon 34 which has been inserted around a conventional guide wire 10 in which an exothermic reaction is permitted to occur once the balloon has been inflated to release energy into the surrounding tissue thereby, again, to provide for fusion of the tissue surrounding the inflated balloon.

Figure 7:
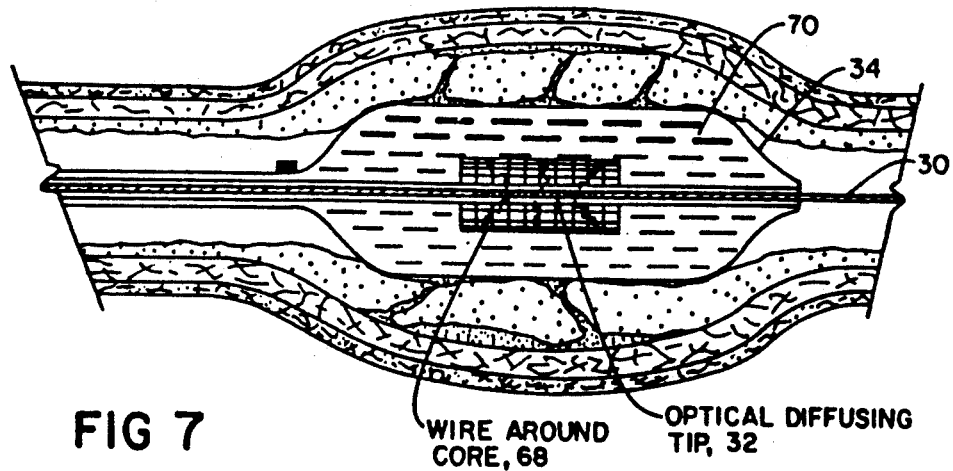
FIG. 7 is a cross-sectional and diagrammatic illustration of an alternative embodiment of the subject invention in which a wire core is provided adjacent an optical diffusing tip with the laser radiation being tuned to a wavelength which heats the wires which then heats the liquid within the balloon which in turn heats the surrounding material to provide the fusion result of FIG. 3.

Referring now to FIG. 7, energy may be introduced to the balloon 34 by virtue of the utilization of optical fiber 30 with diffusing tip 32 which is surrounded by a wire core 68 which may be expandable, adapted to absorb the radiation from the diffusing tip. In this embodiment, the wire made of an absorbing material such as stainless steel, platinum, gold, silver or tungsten and the radiation utilized to heat the wire core is on the order of 0.3 to 10.6 microns in one embodiment. In this embodiment the wire core heats liquid or fluid 70 within the balloon which again transmits heat to the required area for the required fusion.

In another embodiment, the optical fiber terminates in a sleeve or cap of an absorbing material which absorbs the laser energy and heats the liquid.

Figure 8:
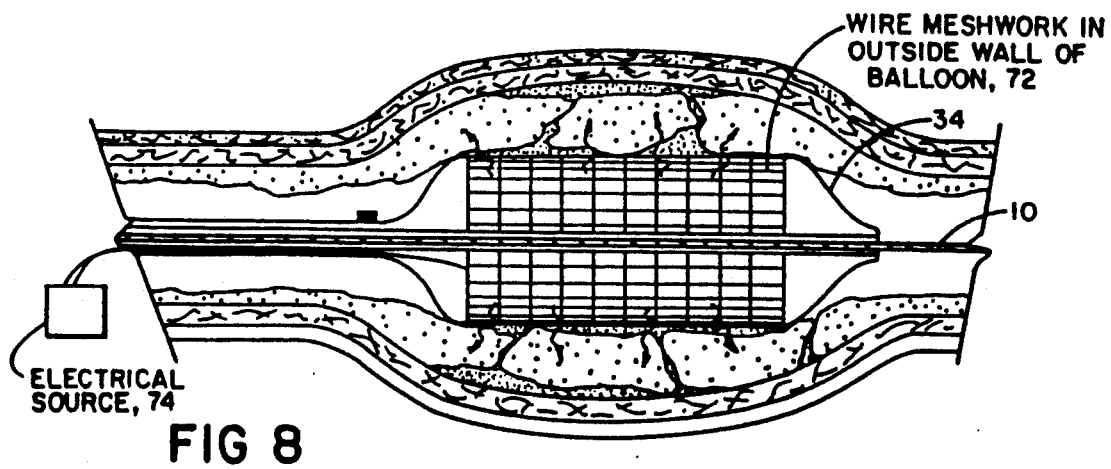
FIG. 8 is a cross-sectional and diagrammatic illustration of another embodiment of the subject invention in which the balloon wall is provided with a network of electrical wires and in which the balloon is heated by virture of the application of electrical energy to the wires which heats the area surrounding the balloon thereby to provide the fusion result of FIG. 3.

Referring to FIG. 8, balloon 34 itself may be provided with a meshwork of electrical wires 72 which are driven by an electrical source 74 which serves to heat the exterior of the balloon once it has been inserted around conventional guide wire 10. In this embodiment, it is the surface of the balloon which is heated directly by the use of electrical energy to produce the aforementioned fusion.

Figure 9:
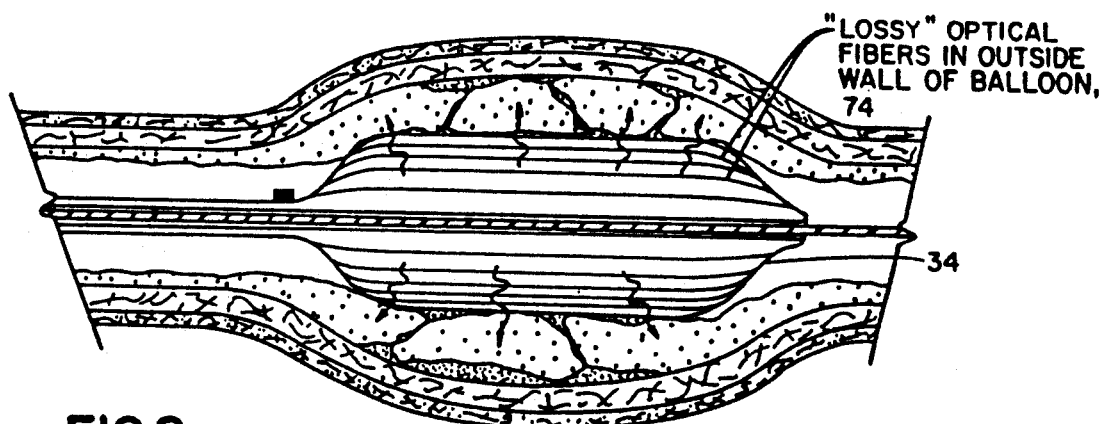
FIG. 9 is a cross-sectional and diagrammatic illustration of another embodiment of the subject invention in which the balloon is provided with a number of "lossy" optical fibers along or adjacent the outside wall of the balloon and in which laser radiation is transmitted through these "lossy" optical fibers, thereby to heat adjacent components either within the balloon or within the coronary artery to provide the fusion result of FIG. 3.

In a still further alternative embodiment and referring now to FIG. 9, the surface of balloon 34 may be provided with "lossy" optical fibers 76 which are driven by laser radiation and which radiate energy in all directions outwardly to the tissue surrounding balloon 34. In such a case, 1.06 micron radiation may be utilized which in turn heats the blood surrounding the inflated balloon thereby causing the aforementioned fusion result of FIG. 3.

Figure 10:
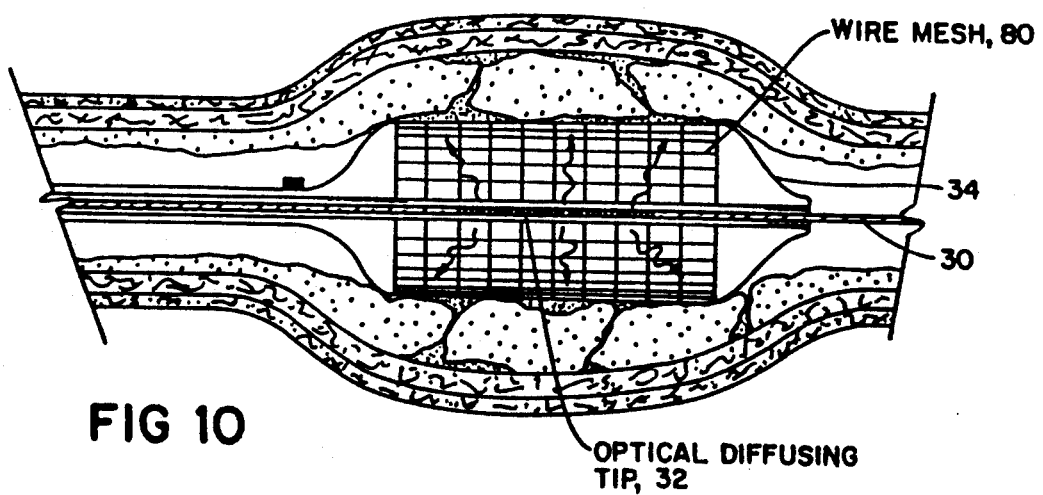
FIG. 10 is a cross-sectional and diagrammatic illustration of another embodiment of the subject invention in which a wire mesh is provided at or adjacent the walls of the balloon and in which an optical diffusing tip is provided with radiation of an energy which is absorbed by the wires thereby to heat the wires and thus the surrounding coronary wall tissue to provide the fusion result of FIG. 3.

In a still further embodiment and referring now to FIG. 10, the exterior or interior of the balloon wall may be provided with a wire mesh 80 which, as in the FIG. 7 embodiment, is heated through diffused radiation from diffusing tip 32 which is located along optical fiber 30. In this embodiment optical radiation is absorbed in the wire mesh which heats up and causes the aforementioned fusion.

The amount of energy delivered to the wall of the balloon and the surrounding tissue varies from 50 to 1000 joules depending upon the size of the artery and the method of introducing energy into the region. Typically, in terms of 5 to 20 watts of neodymium: YAG laser power is necessary for 10 to 35 seconds for a balloon having a longitudinal extent of 2 cm, a diameter of 3 mm when the balloon is inflated, and a diffusing tip of one centimeter for irradiating an arterial segment one centimeter in length. When only discrete region(s) within the arterial wall adjacent to the inflated balloon are heated, significantly less energy is necessary to achieve tissue fusion.

Moreover as mentioned above, a special dye may be utilized such that the blood and/or plaque tissue more strongly absorbs light of a given wavelength thereby increasing the chance of fusion while at the same time decreasing the overall time for the procedure.

Referring back now to FIG. 2, an acoustic sensor 100 may be placed adjacent to balloon 34 for the purpose of sensing the sounds produced by the laser irradiation heating of the tissue. A catheter sound transducer similar to the transducer incorporated in an end-tipped manometer catheter for measurement of intravascular pressure is positioned within the outer catheter near the balloon site. If the laser radiation incident on the plaque through the balloon wall is intense enough to cause vaporization, a high frequency acoustic signal is generated which is picked up by the sound transducer and relayed to a control unit 102 which is utilized either to indicate that vaporization has taken place and/or to automatically terminate the emission of laser radiation or other heating source power delivery.

Having above indicated a preferred embodiment of the present invention, it will occur to those skilled in the art that modification and alternative can be practiced within the spirit of the invention. It is accordingly intended to define the scope of the invention only as indicated in the following claims:

What is claimed is:

1. A Method for transluminal angioplasty of a stenosed artery comprising the steps of:

applying sufficient outward pressure to a selected stenosed region of the artery to form an enlarged channel therethrough, the outward pressure being applied with an expandable device; and applying sufficient energy to the stenosed region to cause the stenosed region to be heated sufficiently to substantially maintain said enlarged channel after removal of outward pressure, said energy being applied to substantially the entire circumference of the stenosed region of the artery simultaneously.

2. A method as defined in claim 1 wherein the step of applying energy is performed after sufficient outward pressure has been applied to the stenosed region to form an enlarged channel therethrough.

3. A method for treatment of a body passage comprising the steps of:

expanding an expandable device at a selected site within a body passage to form an enlarged lumen through the body passage; and while the expandable device is expanded to form an enlarged lumen, providing heat to the selected site within the body passage, said heat being provided at a level sufficient to fuse the tissue, said level being below the vaporization threshold of the tissue, and said heat being provided to substantially the entire circumference of the body passage simultaneously.

4. A method for treatment of a body passage comprising the steps of:

expanding a selected region of a body passage with an expandable device to form an enlarged lumen through the body passage; and heating substantially the entire circumference of the selected region simultaneously, the selected region being heated sufficiently to substantially maintain the enlarged lumen after removal of the expandable device.

5. A method as defined in claim 4 wherein said body passage comprises a blood vessel.

6. A method as defined in claim 4 wherein the step of heating the selected region is performed after an enlarged lumen has been formed through the body passage.

7. A method for treatment of a body passage comprising the steps of:

compressing the tissue in a selected region of the body passage with an expandable device; and applying energy to the selected region at a level sufficient to fuse the compressed tissue in the selected region, said level being below the vaporization threshold of the tissue and said energy being applied to substantially the entire circumference of the body passage simultaneously.

* * * * *